United States Patent [19]

Nickell et al.

[11] Patent Number: 4,661,148

[45] Date of Patent: Apr. 28, 1987

[54] PENT-2-EN-4-ON-2-YL 2-(4-(5-TRIFLUOROMETHYL-2-PYRIDINYLOXY)PHENOXY)PROPANOATE USEFUL FOR INCREASING RECOVERABLE SUGAR IN SUGAR CANE

[75] Inventors: Louis G. Nickell, Chicago; Leonard J. Stach, Riverside; Takeo Hokama, Chicago, all of Ill.

[73] Assignee: Sandoz Ltd., Basel, Switzerland

[21] Appl. No.: 766,750

[22] Filed: Aug. 19, 1985

[51] Int. Cl.$^4$ .................... C07D 213/64; A01N 43/40
[52] U.S. Cl. ......................................... 71/94; 546/302
[58] Field of Search ............................ 546/302; 71/94

[56] References Cited

U.S. PATENT DOCUMENTS

| | | | |
|---|---|---|---|
| 4,133,675 | 1/1979 | Schurter et al. | 71/94 |
| 4,233,054 | 11/1980 | Szczepanski et al. | 71/70 |
| 4,280,832 | 7/1981 | Koerwer | 71/94 |

*Primary Examiner*—Alan L. Rotman
*Attorney, Agent, or Firm*—Gerald D. Sharkin; Richard E. Vila

[57] ABSTRACT

The subject matter of this invention is the new compound, pent-2-en-4-on-2-yl 2-[4-(5-trifluoromethyl-2-pyridinyloxy)phenoxy]propanoate. This compound is useful for increasing the recoverable sugar in sugarcane.

3 Claims, No Drawings

PENT-2-EN-4-ON-2-YL 2-(4-(5-TRIFLUOROMETHYL-2-PYRIDINYLOXY)-PHENOXY)PROPANOATE USEFUL FOR INCREASING RECOVERABLE SUGAR IN SUGAR CANE

This invention relates to the new compound, pent-2-en-4-on-2-yl-2-[4-(5-trifluoromethyl-2-pyridinyloxy)-phenoxy]-propanoate and to a method of increasing the yield of sugar obtained from sugarcane and more particularly relates to a method of increasing the recoverable sugar in sugarcane by treating the sugarcane plant during its maturation with this new compound.

A variety of plant growth regulators, stimulants and promotors have been tried in the past in attempts to increase the yields of cultivated crops. It has been found that materials that have an effect on one crop will not necessarily have an effect or have a different effect on other crops.

It has now been found that the recovery of sugar from sugarcane can be significantly increased by the use of certain esters. Consequently it has now been found that it is possible to increase the recoverable sugar in sugarcane by contacting the sugarcane plant with an effective amount of pent-2-en-4-on-2-yl 2-[4-(5-trifluoromethyl-2-pyridinyloxy)phenoxy]propanoate.

This compound can readily be prepared by reacting 2-[4-(5-trifluoromethyl)-2-pyridinyloxy)phenoxy]propionic acid chloride and 2,4-pentanedione as shown in the following example:

EXAMPLE 1

Preparation of Pent-2-en-4-on-2-yl 2-[4-(5-trifluoromethyl-2-pyridinyloxy)phenoxy]-propanoate 2-[4-(5-trifluoromethylpyridinyl-2-oxy)phenoxy]-propanoic acid (15 grams) and thionyl chloride (20 ml) were placed into a glass reaction flask with stirrer and heated to 60°-65° C. for one hour and then stripped on a rotoevaporator to remove excess thionyl chloride resulting in the desired product (16.5 grams).

2.4-Pentanedione (4 grams, 0.04 mol), methylene chloride (100 ml) and triethylamine (3 grams, 0.03 mol) were placed into a 3-necked glass reaction flask equipped with dropping funnel, stirrer, thermometer and a nitrogen inlet line. The mixture was cooled to 5° C. and 2-[4-(5-trifluoromethylpyridinyl-2-oxy)phenoxy]propanoic acid chloride (5.5 grams; 0.015 mol) dissolved in methylene chloride (30 ml) was added dropwise over a 5 minute period. The mixture was then stirred for 1 hour, transferred to a separatory funnel, washed three times with water (60 ml) and passed through phase separating paper. The filtrate was concentrated to a red oil (6.5 grams). The concentrate was chromatographed through Florisil clay, 60–100 mesh, and eluted with hexane-ethyl acetate. Fractions 8–12 gave the desired product as a yellow gum. Elemental analysis results were as follows:

|  | Theoretical (%) | Found (%) |
|---|---|---|
| Carbon: | 58.68 | 58.62 |
| Hydrogen: | 4.43 | 4.51 |
| Nitrogen: | 3.42 | 3.40 |

The effectiveness of this compound for increasing the recoverable sugar in sugarcane is demonstrated by the following test, the cane was harvested 8 weeks after application of the compound.

The top 14 joints of the treated cane as well as those of the controls were removed, combined and analyzed for juice purity and pol percent cane, following the "press method" developed and described by T. Tanimoto, Hawaiian Planter Record, 57, 133 (1964). Pol percent cane is a polarimetric determination and equals the percentage of sucrose if the latter is the only substance in the solution which will rotate the plane of polarized light. The pol percent cane is a standard method of determining the sucrose content of sugarcane.

| Compound of | Rate of Application (lbs./acre) | Pol % Cane | Juice Purity |
|---|---|---|---|
| Example 1 | 1 | 13.10 | 85.39 |
| Control | 0 | 10.09 | 78.37 |

In the use of this compound to increase the recoverable sugar in sugarcane, sugarcane is treated at a late stage of development of the sugarcane wherein most of the sugar formation takes place. Thus, under normal growing conditions and common cultivation practices the active compound of this invention can be applied to the sugarcane during the period of from about 2 to about 10 weeks before harvesting.

The amount of active compound required to effectively increase the recoverable sugar from sugarcane can vary somewhat depending on such factors as the time of application, the weather, crop density, method of application and the like. Generally, an amount of at least 0.1 pounds per acre and preferably an amount of from 0.1 pounds per acre to about 10 pounds per acre can be used. While an amount greater than those mentioned can be used, they will not result in an advantage that would warrant their expense and are, therefore, not practical.

For practical use in treating sugarcane, the active compounds of this invention are generally incorporated into compositions or formulations which comprise an inert carrier and an effective amount of the compound. The compositions enable the active compound to be conveniently applied to the sugarcane at the desired rate. The formulations can be liquid formulations such as emulsifiable concentrates or solutions or solid formulations such as dusts, granules or wettable powders.

The preferred compositions are liquid formulations, particularly solutions or emulsifiable concentrates. Emulsifiable concentrates comprise the active compound, according to this invention, and as the inert carrier, a solvent and an emulsifier. Such emulsifiable concentrates can be extended with water and/or oil to any desired concentration of active compound for application as sprays to the sugarcane. The emulsifier most commonly used in these concentrates are nonionic or mixtures of nonionic with anionic surface-active agents. With the use of some emulsifier systems an inverted emulsion (water-in-oil) can be prepared.

Typical formulations according to the present invention useful for increasing the recoverable sugar in sugarcane are illustrated in the following examples wherein the quantities are given in parts by weight.

EXAMPLE 2

Preparation of an Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

| | |
|---|---|
| Product of EXAMPLE 1 | 25 |
| Sodium lauryl sulfate | .2 |
| Sodium lignin sulfate | 3 |
| Kerosene | 70 |

EXAMPLE 3

Preparation of a Wettable Powder

The following components are mixed intimately in conventional mixing or blending equipment and are then ground to a powder having a particle size of less than about 50 microns. The finished powder is dispersed in water to give the desired concentration of active compound for application to the sugarcane.

| | |
|---|---|
| Product of EXAMPLE 1 | 50 |
| Fuller's earth | 47 |
| Sodium lauryl sulfate | 2.5 |
| Methyl cellulose | 0.5 |

EXAMPLE 4

Preparation of a Dust

The following ingredients are mixed thoroughly and are then ground to an average particle size of less than about 50 microns to give a dust suitable for application with conventional dusting equipment.

| | |
|---|---|
| Product of EXAMPLE 1 | 10 |
| Powdered talc | 90 |

The effectiveness of the compounds of this invention for increasing the recoverable sugar from sugarcane was demonstrated in a field test by applying a solution in acetone diluted for application to the various indicated application rates. The test compound was applied at each rate on the spindle area of each of 20 stalks of sugarcane in a field in Hawaii, using a syringe with a fine needle as the applicator. A set of 10 of these treated stalks from each group was harvested at 4 and 8 weeks after such treatment. In each harvest a set of 10 untreated stalks were also harvested as a control.

We claim:

1. The compound, pent-2-en-4-on-2-yl 2-[4(5-trifluoromethyl-2-pyridinyloxy)phenoxy]propanoate.

2. A method for increasing the recoverable sugar contained in sugarcane which comprises contacting the sugar cane plant from 2 to 10 weeks before harvest with a recoverable sugar-enhancing effective amount of the compound of claim 1.

3. The method of claim 2 wherein the sugarcane is contacted with from about 0.1 to about 10 pounds of the compound of claim 1.

* * * * *